(12) United States Patent
Cuello et al.

(10) Patent No.: US 12,139,698 B2
(45) Date of Patent: Nov. 12, 2024

(54) AXIAL DISPERSION BIOREACTOR (ADBR) FOR PRODUCTION OF MICROALGAE AND OTHER MICROORGANISMS

(71) Applicant: ARIZONA BOARD OF REGENTS ON BEHALF OF THE UNIVERSITY OF ARIZONA, Tucson, AZ (US)

(72) Inventors: Joel L. Cuello, Tucson, AZ (US); Yaser Mehdipour, Tucson, AZ (US); Andres P. Mayol, Tucson, AZ (US); Shiwei He, Tucson, AZ (US); Chen-Han Shih, Tucson, AZ (US); Lawrence Victor Vitug, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 504 days.

(21) Appl. No.: 16/956,895

(22) PCT Filed: Dec. 21, 2018

(86) PCT No.: PCT/US2018/067106
§ 371 (c)(1),
(2) Date: Jun. 22, 2020

(87) PCT Pub. No.: WO2019/126654
PCT Pub. Date: Jun. 27, 2019

(65) Prior Publication Data
US 2020/0318052 A1 Oct. 8, 2020

Related U.S. Application Data

(60) Provisional application No. 62/609,780, filed on Dec. 22, 2017.

(51) Int. Cl.
*C12M 1/06* (2006.01)
*B01J 19/00* (2006.01)
*C12M 1/00* (2006.01)

(52) U.S. Cl.
CPC .......... *C12M 27/02* (2013.01); *B01J 19/0066* (2013.01); *C12M 27/22* (2013.01); *C12M 29/06* (2013.01)

(58) Field of Classification Search
None
See application file for complete search history.

(56) References Cited

U.S. PATENT DOCUMENTS 98,161 A * 12/1869 Gregory ................ B01F 31/441
366/258
328,188 A * 10/1885 Clark .................... B01F 31/441
366/335

(Continued)

FOREIGN PATENT DOCUMENTS

AT 515084 B1 * 6/2015 ............. B01F 11/00
CN 111758542 A 10/2020

(Continued)

OTHER PUBLICATIONS

Nayar, Gautam. Oxygen transport in animal cell biogreactors with vibrating-plate aerators. Diss. Massachusetts Institute of Technology, 1995.

(Continued)

*Primary Examiner* — William H. Beisner
(74) *Attorney, Agent, or Firm* — NGUYEN TARBET IP LAW

(57) ABSTRACT

An Axial Dispersion Bioreactor (ADBR) is designed for the photoautotrophic, mixotrophic or heterotrophic growth and production of microalgae and other microorganisms (bacteria, fungi, etc.) as well as cell cultures of plants, animals, insects and others. The ADBR is equipped with a plate (Continued)

having a plurality of holes that moves longitudinally or axially within the bioreactor to effect superior hydrodynamic and mixing patterns. The ADBR has the advantages of providing a low-shear culture environment, superior liquid mixing, and efficient gas mass transfer.

20 Claims, 10 Drawing Sheets

(56) References Cited

U.S. PATENT DOCUMENTS

| | | | |
|---|---|---|---|
| 600,978 A * | 3/1898 | Hawk | B01F 31/441 366/332 |
| 980,824 A * | 1/1911 | Noakes | B01F 31/441 366/256 |
| 1,124,855 A | 1/1915 | Callow et al. | |
| 1,308,587 A | 7/1919 | Heuser | |
| 1,383,881 A | 7/1921 | Thomas | |
| 2,041,184 A | 5/1936 | Isenhour | |
| 2,121,458 A | 6/1938 | Vogelbusch | |
| 3,108,146 A | 10/1963 | Gross | |
| 3,186,644 A | 6/1965 | Ross et al. | |
| 3,266,782 A * | 8/1966 | Gatsis | B01F 31/441 366/335 |
| 3,407,044 A | 10/1968 | Buck | |
| 3,630,498 A | 12/1971 | Bielinksi | |
| 3,779,531 A | 12/1973 | White | |
| 3,867,488 A | 2/1975 | Porterfield | |
| 3,911,064 A | 10/1975 | McWhirter et al. | |
| 3,997,447 A | 12/1976 | Breton et al. | |
| 4,193,950 A | 3/1980 | Stockner et al. | |
| 4,231,974 A | 11/1980 | Engelbrecht et al. | |
| 4,371,480 A | 2/1983 | Vos | |
| 4,465,645 A | 8/1984 | Kaelin | |
| 4,656,138 A | 4/1987 | Redikultsev et al. | |
| 4,779,990 A | 10/1988 | Hjort et al. | |
| 5,023,044 A | 7/1991 | Negron | |
| 5,073,262 A | 12/1991 | Ahlberg et al. | |
| 5,282,681 A | 2/1994 | Supelak | |
| 5,681,509 A | 10/1997 | Bailey | |
| 5,813,760 A * | 9/1998 | Strong | B01F 31/441 366/605 |
| 6,491,422 B1 * | 12/2002 | Rutten | B01F 31/85 366/601 |
| 6,955,462 B1 * | 10/2005 | Davies | B01F 31/441 366/256 |
| 7,086,778 B2 | 8/2006 | Terentiev | |
| 7,459,074 B1 | 12/2008 | Sanchez | |
| 8,151,518 B2 | 4/2012 | Adams et al. | |
| 8,181,387 B2 | 5/2012 | Loeb et al. | |
| 8,651,766 B2 | 2/2014 | Kortmann | |
| 9,670,446 B2 | 6/2017 | Khan | |
| 2005/0218071 A1 | 10/2005 | Austin et al. | |
| 2007/0253288 A1 * | 11/2007 | Mennenga | B01F 31/449 366/274 |
| 2009/0141586 A1 | 6/2009 | Dyer, III | |
| 2009/0277083 A1 | 11/2009 | Barnes | |
| 2009/0293357 A1 | 12/2009 | Vickers et al. | |
| 2011/0058448 A1 * | 3/2011 | Reif | B01F 35/513 366/250 |
| 2012/0060416 A1 | 3/2012 | Brusatore | |
| 2012/0231527 A1 * | 9/2012 | Dubois-Calero | C12M 27/02 435/267 |
| 2014/0079639 A1 | 3/2014 | McDaniel | |
| 2014/0083004 A1 | 3/2014 | Mackenzie | |
| 2015/0218254 A1 | 8/2015 | Sabbadini et al. | |
| 2015/0373935 A1 | 12/2015 | Anderson et al. | |
| 2016/0130547 A1 * | 5/2016 | Venkataramu | B01F 31/441 435/286.7 |
| 2016/0262324 A1 | 9/2016 | Yamane | |
| 2017/0266632 A1 | 9/2017 | Mattson et al. | |
| 2018/0007841 A1 | 1/2018 | Gibson et al. | |
| 2018/0010082 A1 | 1/2018 | Jaques et al. | |
| 2018/0014485 A1 | 1/2018 | Whitcher et al. | |
| 2018/0237734 A1 | 8/2018 | Uller | |
| 2020/0131463 A1 | 4/2020 | Mahajan et al. | |

FOREIGN PATENT DOCUMENTS

| | | | | |
|---|---|---|---|---|
| CN | 212283729 U | | 1/2021 | |
| DE | 202017102656 U1 * | | 8/2017 | |
| EP | 2644025 A1 | | 10/2013 | |
| JP | 2010100795 A | | 5/2010 | |
| JP | 5325272 B2 | | 10/2013 | |
| KR | 20010100277 A * | | 11/2001 | C12M 1/06 |
| KR | 20160053399 A | | 5/2016 | |
| KR | 102161188 B1 | | 9/2020 | |
| KR | 20210081775 A | | 7/2021 | |
| WO | WO2007045678 A1 | | 4/2007 | |
| WO | 2020252364 A1 | | 12/2020 | |
| WO | 2021022169 A1 | | 2/2021 | |

OTHER PUBLICATIONS

Karimi et al. "Oxygen mass transfer in a stirred tank bioreactor using different impeller configurations for environmental purposes." Iranian journal of environmental health science & engineering 10.1 (2013): 1-9.

https://encyclopedia.che.engin.umich.edu/slurry/.

McKenna, P. Electroshocking plants brings chemical rewards. New Scientist. Mar. 28, 2008. 1-2.

Kim et al. Enhancement of mircoalga Haematococcus pluvialis growth and astaxanthin production by electrical treatment. Biosource Technology 268. Jun. 15, 2018. 815-819. Elsevier Ltd.

Kaimoyo et al. Sub-lethal level of Electric Current Elicit the Biosynthesis of Plant Secondary Metabolites. Biotechnol. Prog. 2008, 24, 377-384.

Cuello et al. Ebb-and-Flow Bioreactor Regime and Electrical Elicitation: Novel Strategies for Hairy Root Biochemical Production. Electronic Journal of Integrative Biosciences 3(1): 45-56. Arkansas State University.

Pullagurala et al. "Plant uptake and translocation of contaminants of emerging concern in soil." Science of the Total Environment 636 (Sep. 15, 2018): 1585-1596. Abstract, p. 1592 col. 2 para 3; p. 1594 col. 1 para 3; Figure 2.

Kurade et al. "Uptake and biodegradation of emerging contaminant sulfamethoxazole from aqueous phase using lpomoea aquatica." Chemosphere 225 (Jun. 1, 2019): 696-704. Entire Document.

Recsetar et al. "Evaluation of a Recirculating Hydroponic Bed Bioreactor for Removal of Contaminants of Emerging Concern from Tertiary-Treated Wastewater Effluent." Chemosphere (Sep. 11, 2020): 128121. Entire Document.

Morrow, R. C., and T. M. Crabb. "Biomass production system (BPS) plant growth unit." Advances in Space Research 26.2 (2000): 289-298.

Porterfield et al. "A ground-based comparison of nutrient delivery technologies originally developed for growing plants In the spaceflight environment." HortTechnology 10.1 (2000): 179-185.

Dreschel et al. "Examining Dehydration and Hypoxic Stress in Wheat Plants Using a Porous Tube Plant Nutrient Delivery System Developed for Microgravity." International Conference on Environmental Systems. No. O5ICES-64. 2005.

(ISA/210) International Search Report and (ISA/237) Written Opinion of the International Searching Authority, PCT/US23/72838, uploaded Jan. 19, 2024.

* cited by examiner

Single Circular Plate  Double/Multiple Circular Plates

Double/Multiple Rectangular Plates

Single Curved Plate  Double/Multiple Curved Plates

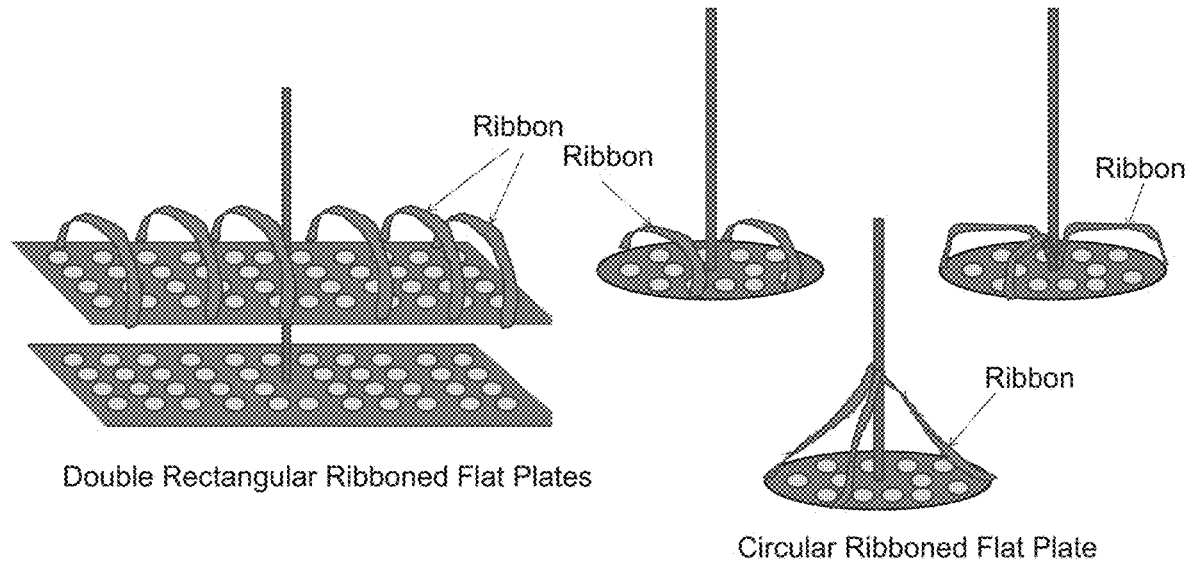
FIG. 11A  FIG. 11B
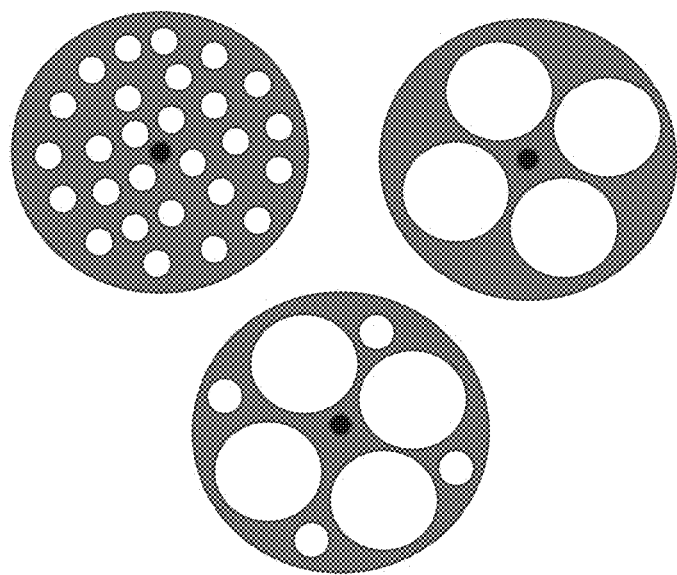
FIG. 12

AXIAL DISPERSION BIOREACTOR (ADBR) FOR PRODUCTION OF MICROALGAE AND OTHER MICROORGANISMS

CROSS-REFERENCES TO RELATED APPLICATIONS

This application claims priority to U.S. Provisional Patent Application No. 62/609,780, filed Dec. 22, 2017, the specification(s) of which is/are incorporated herein in their entirety by reference.

BACKGROUND OF THE INVENTION

Field of the Invention

The present invention relates to a bioreactor designed specifically for the photoautotrophic, mixotrophic, or heterotrophic growth and production of microalgae and other microorganisms such as bacteria and fungi, as well as cell cultures of plants, animals, insects, and others.

The photoautotrophic growth of microorganisms or cells is enabled by the photosynthetic capacity of the chlorophyll-containing microorganisms or cells, whereby carbon dioxide ($CO_2$), through photosynthetic carbon fixation, serves as the carbon (or food) source. Photoautotrophic growth requires the presence of light for photosynthesis to occur. A steady supply of $CO_2$ when light is available also promotes culture growth.

By contrast, heterotrophic growth takes place when the microorganisms or cells, in the absence of photosynthetic $CO_2$ fixation, rely on exogenous carbon-based molecules, typically sugars such as glucose or sucrose, present in the liquid culture medium as their carbon (or food) source. Heterotrophic growth necessitates a sterile or axenic growth environment to avoid culture contamination; otherwise, unwanted and competing bacteria and other microorganism would grow in the culture owing to the presence of the carbon-based food source. This mode of growth also requires a steady supply of oxygen ($O_2$) which the microorganisms or cells need as they breakdown the carbon-based molecules through the process of respiration. Since light is not essential, heterotrophic production is generally carried out in darkness.

Mixotrophic growth takes place when the microorganisms or cells grow both photo-autotrophically and hetero-trophically. Any of the three types of growth can take place in a bioreactor. A bioreactor can be defined as a vessel or body in which biological reactions are carried out by microorganisms, or enzymes they produce, contained within the reactor itself. The main objective in the design of a bioreactor is to generate an optimal environment for the desired biological process to take place on a large and economic scale.

Description of Related Art Including Information Disclosed

A primary design feature of bioreactors is to provide proper mixing of the liquid in the vessel so as to approach a well-mixed condition, thereby ensuring that both dissolved nutrients and gases are distributed uniformly throughout the reaction volume and that every cell growing in the vessel has adequate physical access to the nutrients and gases. As a corollary, a well-mixed condition will enable and provide necessary gas transfer in the vessel. As heterotrophic cells grow, for instance, they use up oxygen and produce carbon dioxide. The bioreactor must be designed to ensure efficient transfer of oxygen into the culture while allowing efficient removal of carbon dioxide. In the case of photoautotrophic cells, they consume carbon dioxide in the presence of light and produce oxygen. The bioreactor must be designed to ensure efficient transfer of carbon dioxide into the culture while allowing efficient removal of oxygen.

For relatively shear-sensitive cell cultures such as microalgae and plant cells, bioreactors where liquid mixing and gas transfer are accomplished through sparging or bubbling of compressed air containing oxygen and/or carbon dioxide are typically preferred. These so-called pneumatic-type bioreactors include bubble-column, flat-plate and air-lift bioreactors. These bioreactors nonetheless generally suffer from inefficiencies in both liquid mixing and gas transfer as well as significantly increased energy consumption upon scale up. Stirred tank reactors, though having a capacity to achieve a well-mixed liquid condition, nonetheless generally suffer from having a high-shear culture environment and high energy costs.

BRIEF SUMMARY OF THE INVENTION

It is an objective of the present invention to provide systems and methods that allow for the photoautotrophic, mixotrophic, or heterotrophic growth and production of microalgae and other microorganisms such as bacteria and fungi, as well as cell cultures of plants, animals, insects, and others, as specified in the independent claims. Embodiments of the invention are given in the dependent claims. Embodiments of the present invention can be freely combined with each other if they are not mutually exclusive.

In one aspect, the present invention features an Axial Dispersion Bioreactor (ADBR) that may be used for universal applications in biotechnology, pharmaceutical and food industries in the cultivation of microorganisms (algae, bacteria, fungi, etc.) and cell cultures (plant, animal, insect, etc.).

The present invention features a bioreactor system comprising: 1) a bioreactor vessel for containing a fluid; 2) at least one mixer comprising a surface having a plurality of holes disposed through the surface; and 3) a mechanism for moving at least one mixer within the bioreactor vessel. This system allows for the movement of at least one mixer enabling mixing of a fluid in the bioreactor vessel to generate a hydrodynamic flow pattern.

The present invention further features a bioreactor system for the cultivation of biological cultures. The bioreactor system comprises: 1) a bioreactor vessel, comprising a bottom and one or more sidewalls; 2) one or more mixing plates, each comprising a plurality of through holes, wherein the one or more mixing plates are configured to move longitudinally or axially within the bioreactor vessel; and 3) a mechanism for moving the one or more mixing plates longitudinally or axially within the bioreactor vessel. This system allows for the movement of the one or more mixing plates enabling the mixing of a liquid growth medium and the generation of a hydrodynamic flow pattern.

In some aspects, the present invention features varying combinations of: (1) an ADBR plate, whose surface may be flat, zigzag, curved, etc., to effect axial dispersion or mixing within the bioreactor; (2) an ADBR plate of varying geometric configuration, including circular, rectangular, square, elliptical, etc.; (3) an ADBR plate with various patterns of holes, whose geometric shapes and sizes may be uniform or variable; (4) single or multiple ADBR plates; (5) varying plate spacing in the case of multiple ADBR plates; and (6)

ribbons, either rigid or flexible, attached to the ADBR plates to modify or enhance mixing patterns. One of the unique, inventive technical features of the present invention is the mixing plate having a plurality of holes. Without wishing to limit the invention to any theory or mechanism, it is believed that this technical feature of the present invention advantageously provides for a low-shear culture environment, superior liquid mixing, efficient gas mass transfer, and modification and enhancement of the resulting hydrodynamic patterns and mixing of the liquid medium.

None of the presently known prior references or work has the unique inventive technical feature of the present invention. Furthermore, the prior art teaches away from the present invention. For example, the prior art teaches only to use solid and hard-surfaced impellers that rotate or use sparged bubbles to cause the liquid mixing or both. In the case of the present invention, the ADBR plate features, for example, a rigid flat solid surface with holes which, instead of rotating, moves linearly along the axis of the bioreactor, creating a variety of novel hydrodynamic mixing patterns in the bulk liquid in the bioreactor. The geometry, size, number, and distribution of the holes in the ADBR plate are also designed to generate unique hydrodynamic mixing patterns. Further, the use of flexible ribbons in combination with the hard, perforated plates also produces additional novel hydrodynamic mixing patterns. The foregoing could also be used in combination with sparged bubbles from the bottom or other locations in the ADBR.

Other independent design variables to effect optimal hydrodynamic or mixing patterns within the bioreactor include: (7) the rate of back-and-forth axial displacement of the ADBR plate(s); (8) the continuous or intermittent back-and-forth axial displacement of the ADBR plate(s); (9) presence or absence of gas sparging from the bottom of the bioreactor; (10) the use of varying bubble sizes and gas flow rates for gas sparging; (11) the use of varying positions for the sparger(s) at the bottom of the bioreactor; (12) the use of different materials or combinations of materials for bioreactor vessel and ADBR plates; and (13) the use of varying geometric configurations for the vessel, including rectangular box, square box, cylindrical, elliptical, etc.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE SEVERAL VIEWS OF THE DRAWING(S)

The features and advantages of the present invention will become apparent from a consideration of the following detailed description presented in connection with the accompanying drawings in which:

FIGS. 11A and 11B show non-limiting embodiments of rigid or flexible ribbons attached to the ADBR plate in various patterns to modify or enhance the resulting hydrodynamic patterns or mixing of the liquid medium.

FIG. 12 shows non-limiting embodiments of the ADBR plate with varying hole shapes, sizes and patterns.

DESCRIPTION OF PREFERRED EMBODIMENTS

Figure 1:
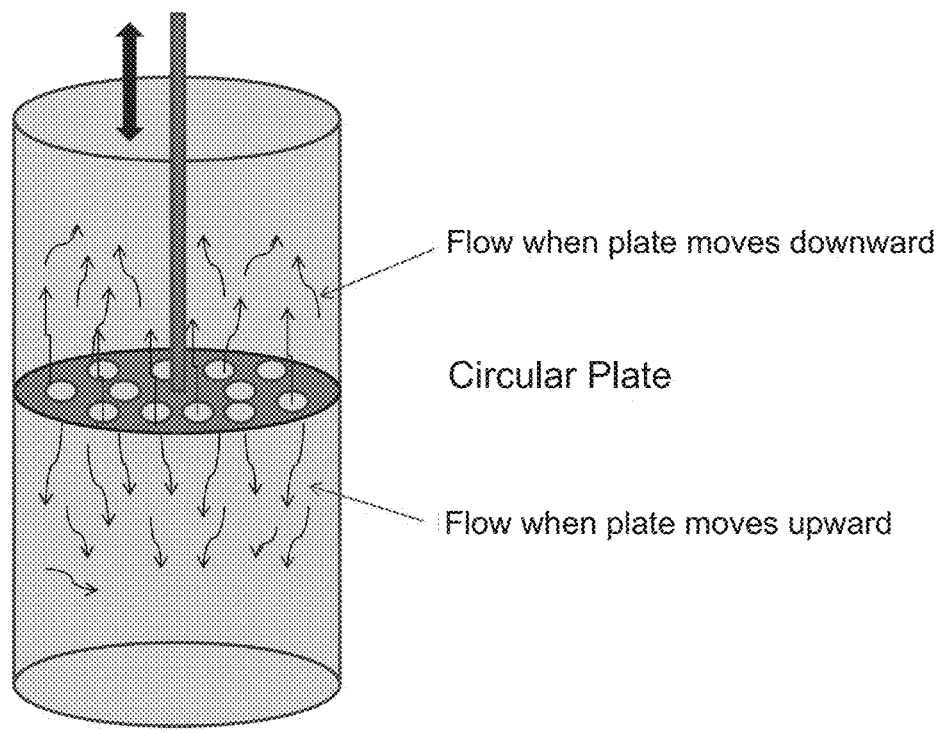
FIG. 1 shows a non-limiting schematic of a cylindrical Axial Dispersion Bioreactor (ADBR) with a perforated plate that moves back and forth along the axial or longitudinal axis of the bioreactor, effecting a hydrodynamic flow pattern and mixing as the liquid medium is forced through the plate holes as the plate moves in either direction.
Figure 2:
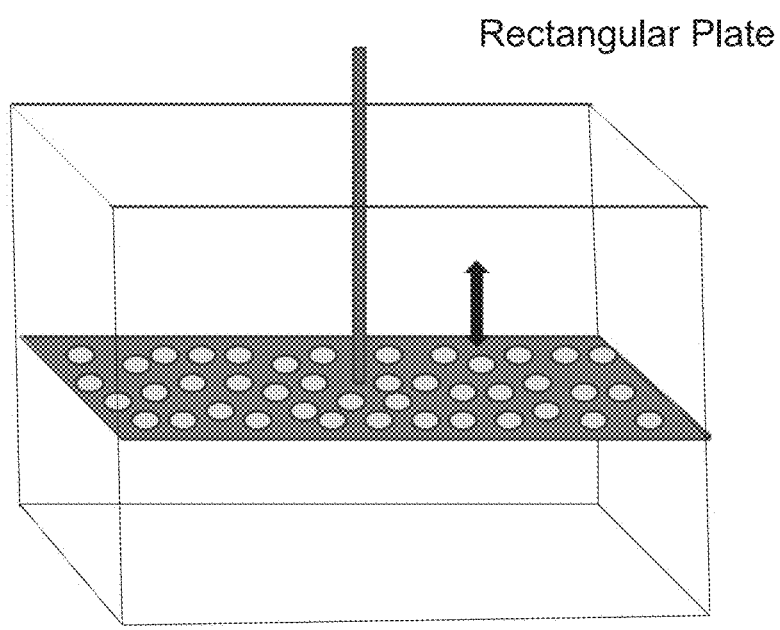
FIG. 2 shows a non-limiting schematic of an ADBR with a rectangular perforated plate that moves back and forth along the axial or longitudinal axis of the bioreactor.

Following is a list of elements corresponding to a particular element referred to herein:
100 Bioreactor
110 Bottom
120 Sidewall
130 Mixing plate
140 Through hole
150 Guide rod (or threaded rod)
160 Mechanism for movement As used herein, the terms "axial" and "longitudinal" are interchangeable. When used in the context of movement, axial or longitudinal movement refers to linear displacement or translation of the plates about a linear path. For example, the plates may move in an up and down motion about an axis within the bioreactor vessel. As another example, in one of the embodiments with the threaded axis, the mechanism of effecting the axial displacement of the plate is by rotating the threaded axial rod. Since the plate may be constrained in place by the walls of bioreactor, the plate then moves linearly along the axis. Reversing the rotation of the threaded axial rod also reverses the direction of the linear displacement of the plate.

As used herein, the terms "radial' and '"cross-sectional" are also synonymous, and are perpendicular to the "axial" and "longitudinal" direction.

Alternatively or in combination, in some embodiments, movements of the ADBR plate may further comprise i) rotating around an axis, ii) moving up and down (vertically) while rotating, and/or iii) moving sideways-horizontally, while optionally rotating and/or moving up and down.

As used herein, hydrodynamic refers to liquid mixing and hydrodynamic flow pattern refers to the resultant pattern of liquid mixing as caused by the movement of the plates.

Referring to FIGS. 1-16, in one embodiment, the present invention features an axial dispersion bioreactor for the cultivation of biological cultures. As a non-limiting example, the bioreactor may comprise: a bioreactor vessel (100) comprising a bottom (110) and one or more sidewalls (120); one or more mixing plates (130), each comprising a plurality of through holes (140); and a mechanism (160) for moving the one or more mixing plates (130) longitudinally or axially within the bioreactor vessel (100). Without wishing to limit the invention to a particular theory or mechanism, the movement of the one or more mixing plates enables the mixing of a liquid growth medium and the generation of a hydrodynamic flow pattern.

In another embodiment, the present invention features a method of promoting the growth and production of a biological culture contained in a bioreactor. As a non-limiting example, the method may comprise: (a) providing a bioreactor, the bioreactor comprising: (i) a bioreactor vessel (100) comprising a bottom (110) and one or more sidewalls (120); (ii) one or more mixing plates (130), each comprising a plurality of through holes (140), wherein the one or more mixing plates (130) are configured to move longitudinally or axially within the bioreactor vessel (100); and (iii) a mechanism (160) for moving the one or more mixing plates (130) longitudinally or axially within the bioreactor vessel (100); (b) providing a biological culture, wherein the biological culture is dispersed within a liquid growth medium; (c) adding the biological culture and liquid growth medium into the bioreactor vessel (100); and (d) moving the one or more mixing plates (130) longitudinally or axially within the bioreactor vessel (100) via the mechanism (160). Preferably, the movement of the one or more mixing plates mixes the liquid growth medium and generates a hydrodynamic flow pattern.

In some embodiments, the bioreactor (a non-limiting example shown in FIG. 16) may be used for photoautotrophic, mixotrophic or heterotrophic growth of a biological culture. In further embodiments, the bioreactor may be used for the growth and production of microalgae, bacteria, fungi, or other microorganisms, as well as cell cultures of plants, animals, insects and others. In still further embodiments, the movement of the one or more mixing plates may be configured to provide a low-shear culture environment, superior liquid mixing, and efficient gas mass transfer.

Figure 9:
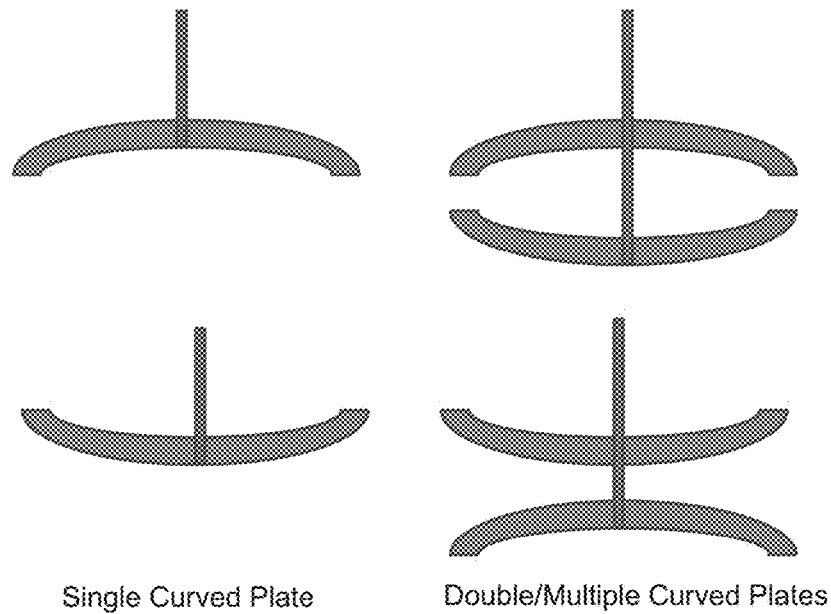
FIG. 9 shows side views of non-limiting embodiments of single and double/multiple ADBR plates assuming curved-surface configurations, and which may be rectangular, square, circular, elliptical, etc., in top-view geometry.
Figure 10:
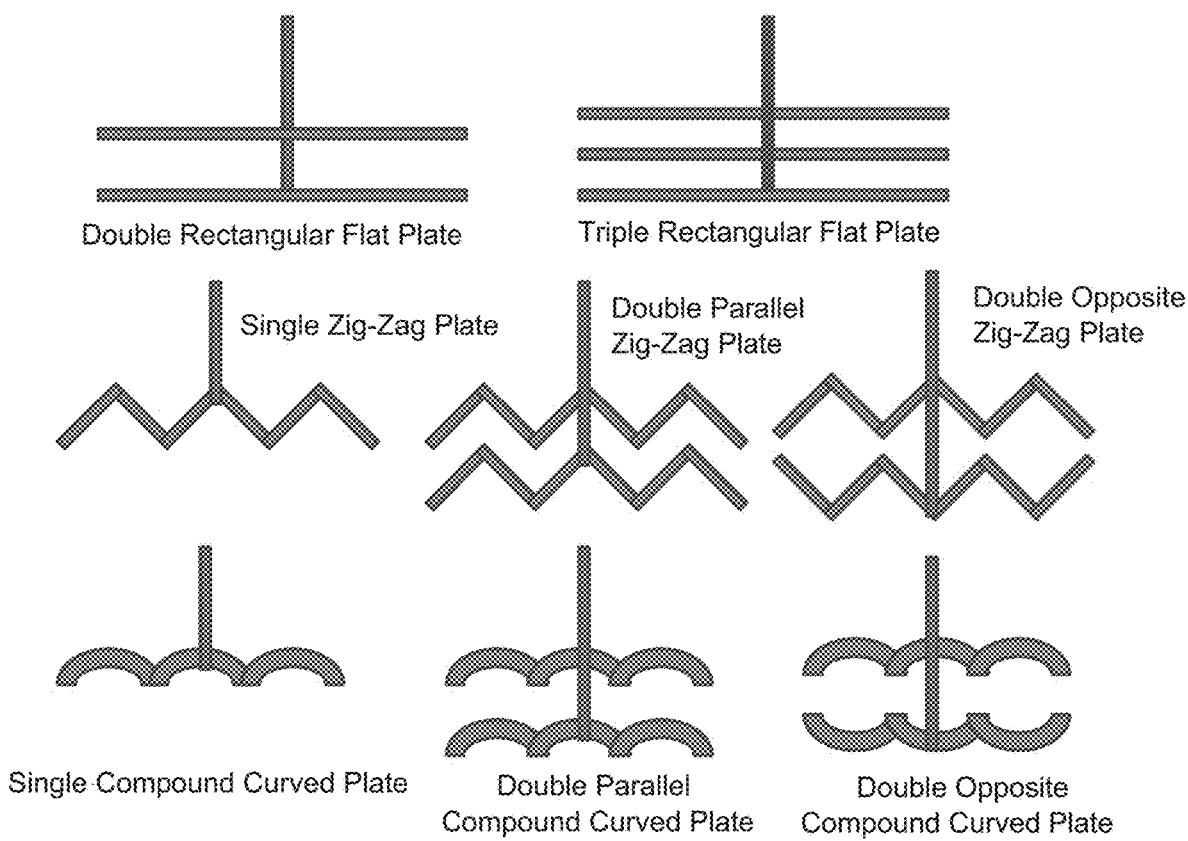
FIG. 10 shows side views of non-limiting embodiments of single and multiple ADBR plates assuming various surface configurations as shown, and which may be rectangular, square, circular, elliptical, etc., in top-view geometry.
Figure 13:
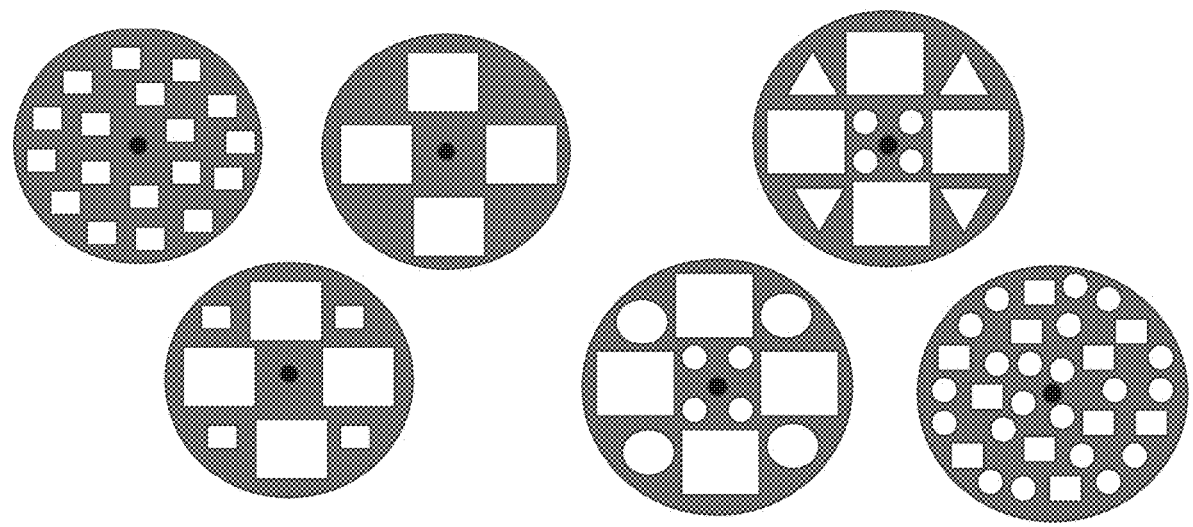
FIG. 13 shows non-limiting embodiments of the ADBR plate with varying hole shapes, sizes and patterns.
Figure 14:
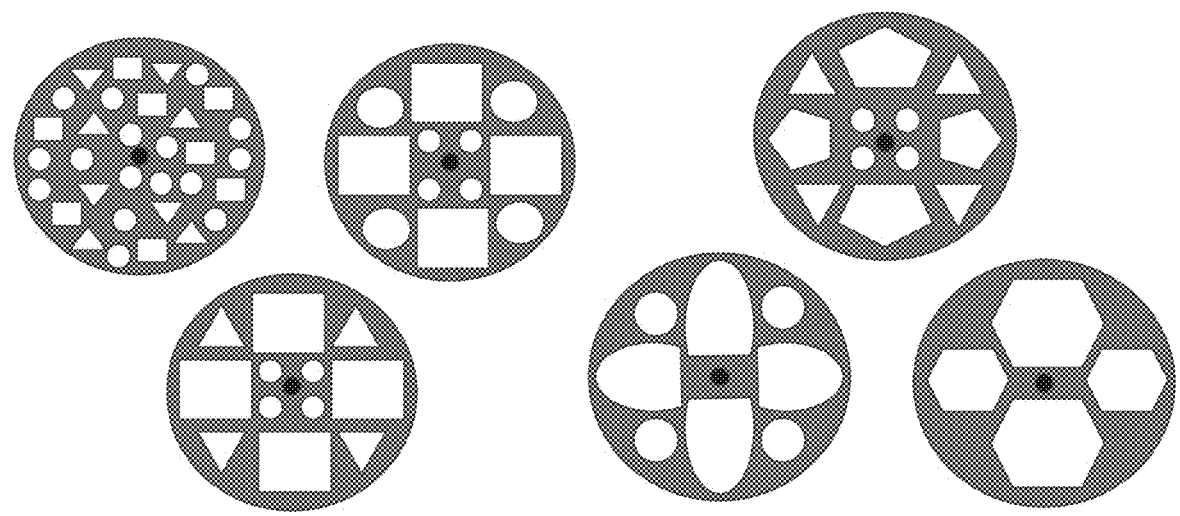
FIG. 14 shows non-limiting embodiments of the ADBR plate with varying hole shapes, sizes and patterns.
Figure 15:
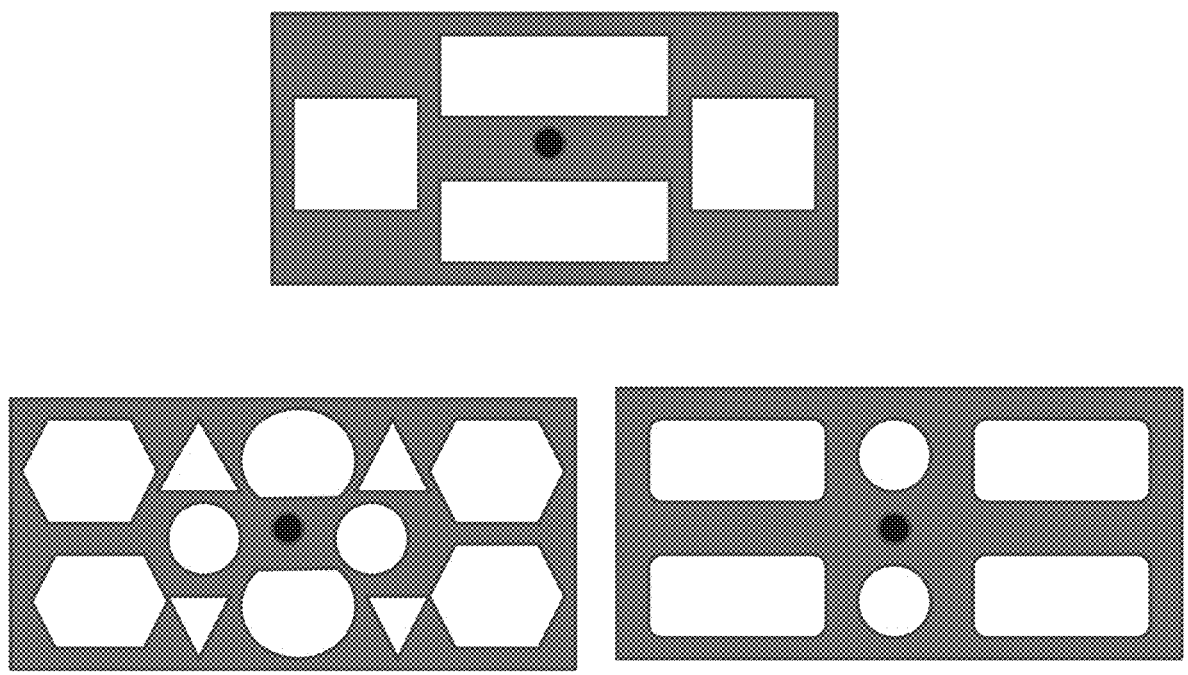
FIG. 15 shows non-limiting embodiments of the ADBR plate with varying hole shapes, sizes and patterns.
Figure 16:
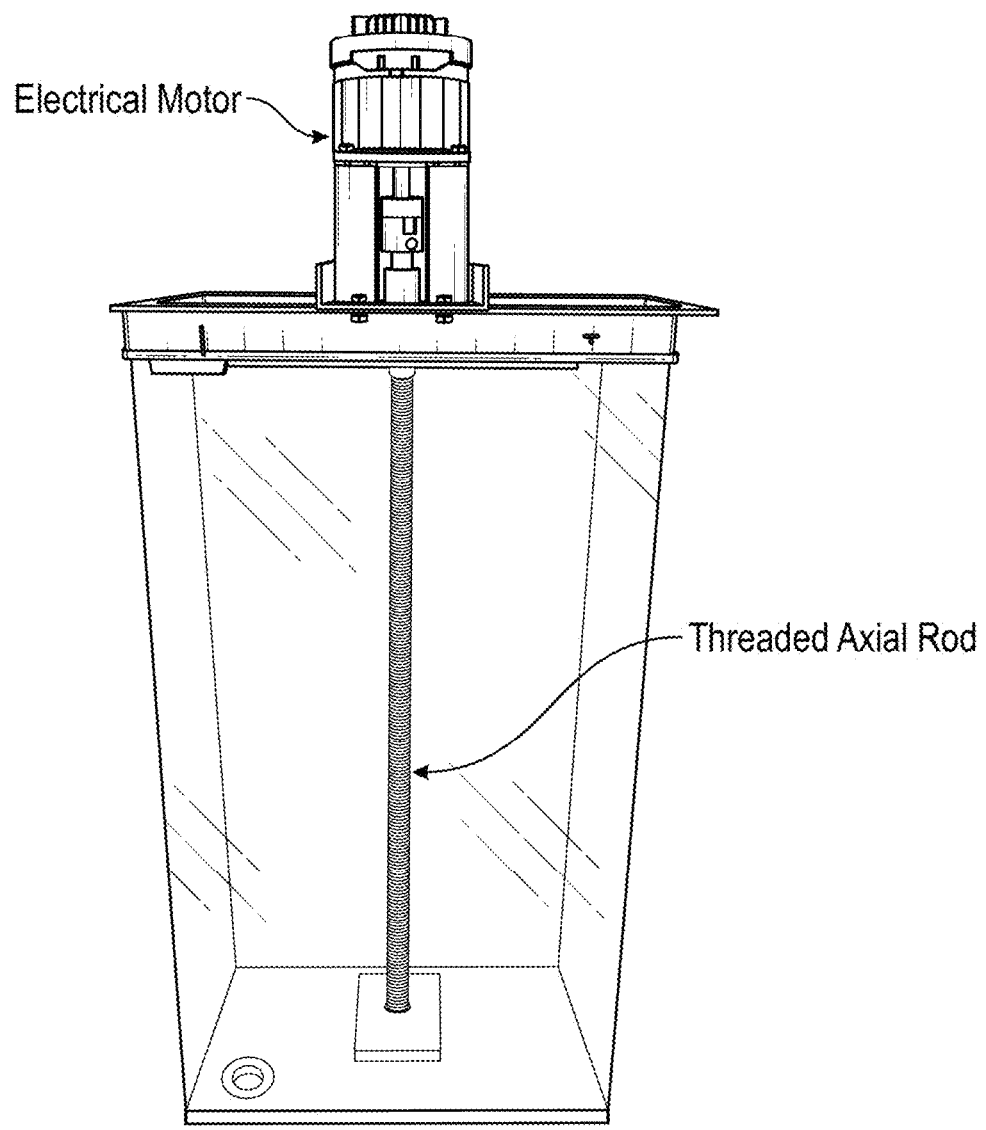
FIG. 16 shows another non-limiting example of the ABDR system.

According to one embodiment, the bottom of the vessel may comprise a shape which gives the vessel a cross-sectional shape, and the one or more mixing plates may comprise a same or different shape. Non-limiting examples of the shapes of the bottom, cross-section, and mixing plates include: a circle, oval, ellipse, square, rectangle, parallelogram, quadrilateral, triangle, pentagon, hexagon, heptagon, octagon, polygon, or irregular shape. In another embodiment, as shown in FIGS. 9-10, the one or more mixing plates may each comprise a surface which is flat, rippled, textured, curved, concaved, convexed, zig-zag patterned, or having compound curves.

In some other embodiments, the plurality of through holes may each comprise a shape and a size. Referring to FIGS. 12-15, the shapes and sizes of the through holes may be uniform or varied. In yet other embodiments, as shown in FIGS. 11A-11B, the bioreactor may comprise a plurality of rigid or flexible ribbons having two ends, wherein the ribbons are attached to the mixing plates at one or both ends. In still other embodiments, the one or more mixing plates may have a spacing between the mixing plates. In preferred embodiments, any or all of (1) the shapes and sizes of the through holes, (2) the density or number per unit area of the through holes, (3) the rigid or flexible ribbons, and (4) the spacing between the one or more mixing plates, may be configured to modify or enhance the hydrodynamic flow pattern or mixing of the liquid growth medium.

In one embodiment, the movement of the one or more mixing plates may be continuous or intermittent back-and-forth axial displacement at a regulated variable rate. In some embodiments, the mixing plates may move back-and-forth in a vertical direction. In other embodiments, the mixing plates may move back-and-forth in a horizontal direction. In another embodiment, one or more gasses are sparged or bubbled through the liquid growth medium from the bottom of the bioreactor with a specified bubble size and a gas flow rate for each gas. Non-limiting example gasses include oxygen, nitrogen, carbon dioxide and carbon monoxide. In yet another embodiment, the one or more sidewalls of the bioreactor may be either transparent or non-transparent. Without wishing to limit the present invention to any particular theory or mechanism, the transparent sidewalls are believed to be advantageous for photoautotrophic and mixotrophic production.

Figure 3:
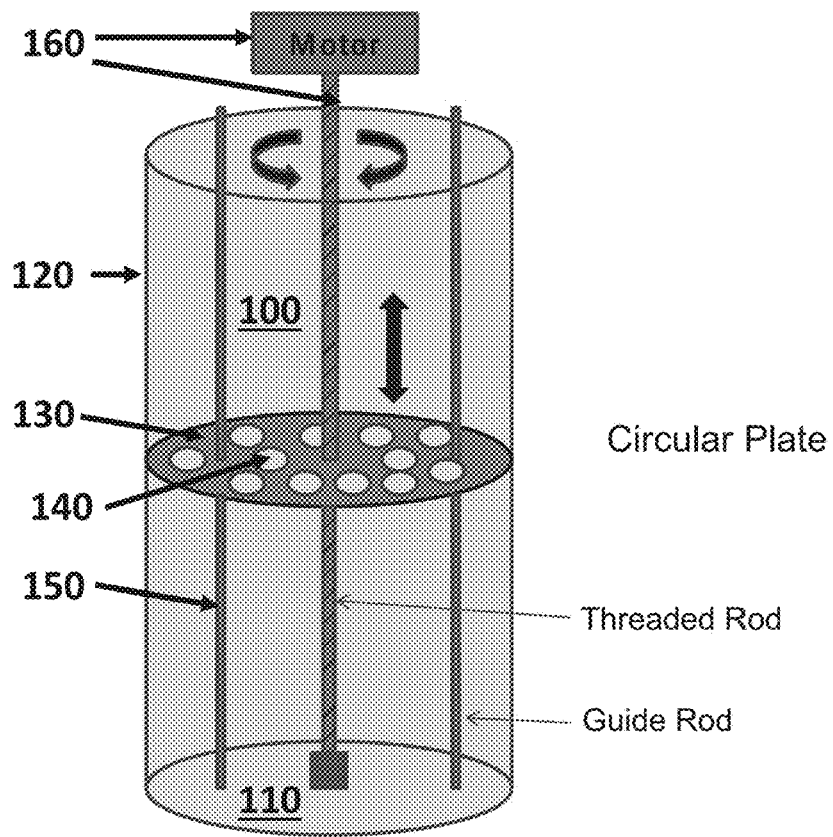
FIG. 3 shows a non-limiting schematic of an ADBR with a cylindrical plate, where the threaded rod rotates in either radial direction to move the plate upward or downward along the axial direction of the bioreactor. The guide rods prevent the plate from spinning or rotating as the threaded rod rotates.
Figure 4:
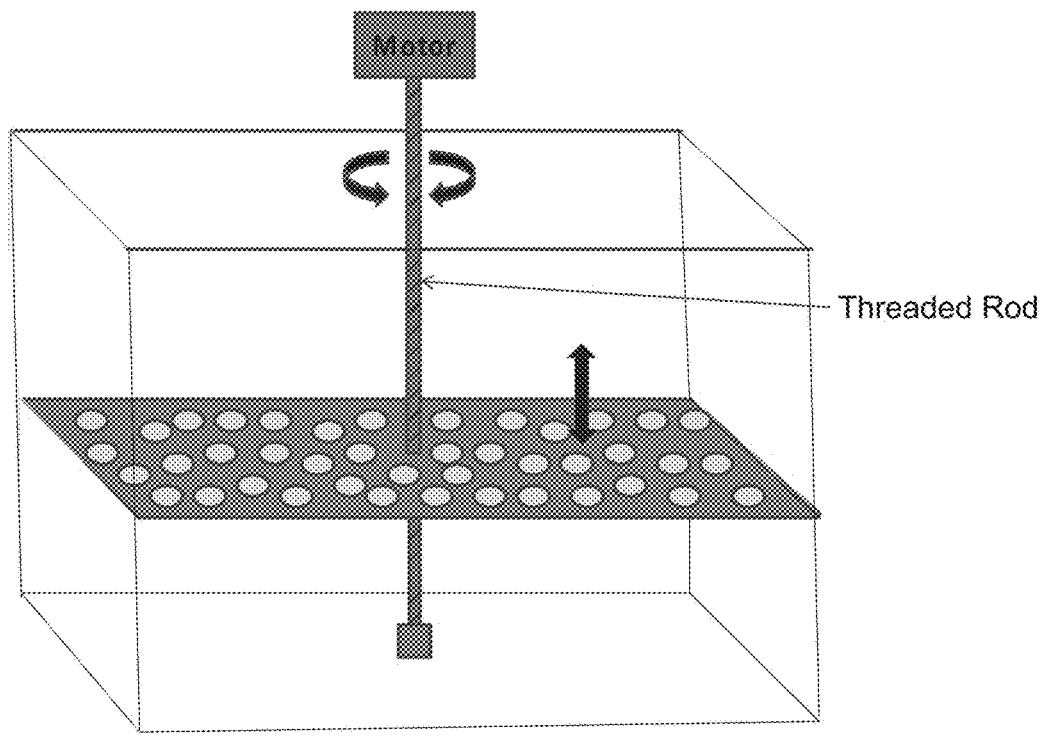
FIG. 4 shows a non-limiting schematic of an ADBR with a rectangular plate, where the threaded rod rotates in either radial direction to move the plate upward or downward along the axial direction of the bioreactor. The right-angled corners of the bioreactor prevent the plate from spinning or rotating as the threaded rod rotates.

In some embodiments, the mechanism for the movement of the one or more mixing plates may comprise a piston rod and crankshaft which connect the one or more mixing plates with an external motor, and wherein the piston rod moves the one or more mixing plates longitudinally or axially within the vessel. As shown in FIGS. 3-4, in other embodiments, the mechanism for the movement of the one or more mixing plates may comprise one or more threaded rods which pass through one or more threaded through holes in the one or more mixing plates and are attached to one or more external motors. In further embodiments, rotation of the one or more mixing plates may be prevented by the shape of the one or more mixing plates and the shape of the cross-section of the vessel, or by use of one or more guide rods (150) configured to fit through one or more holes in the one or more mixing plates. For example, the mechanism of effecting the axial displacement of the plate is by rotating the threaded axial rod. As the plate is constrained in place by the walls of bioreactor, the plate then moves linearly along the axis. Reversing the rotation of the threaded axial rod also reverses the direction of the linear displacement of the plate.

Figure 5:
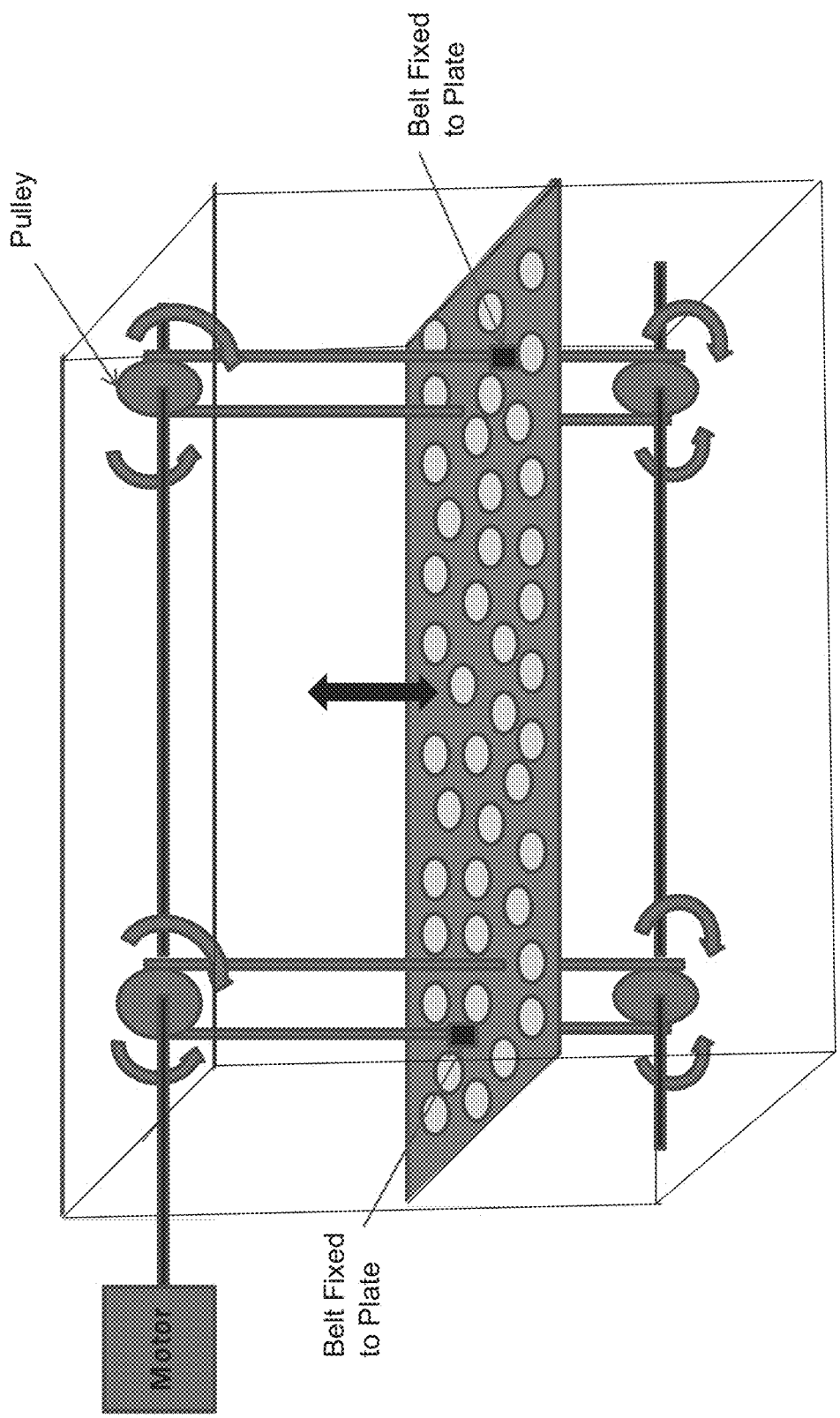
FIG. 5 shows a non-limiting schematic of an ADBR with a rectangular plate, where the pulley systems rotate in either direction to move the plate upward or downward along the axial direction of the bioreactor.
Figure 6A:
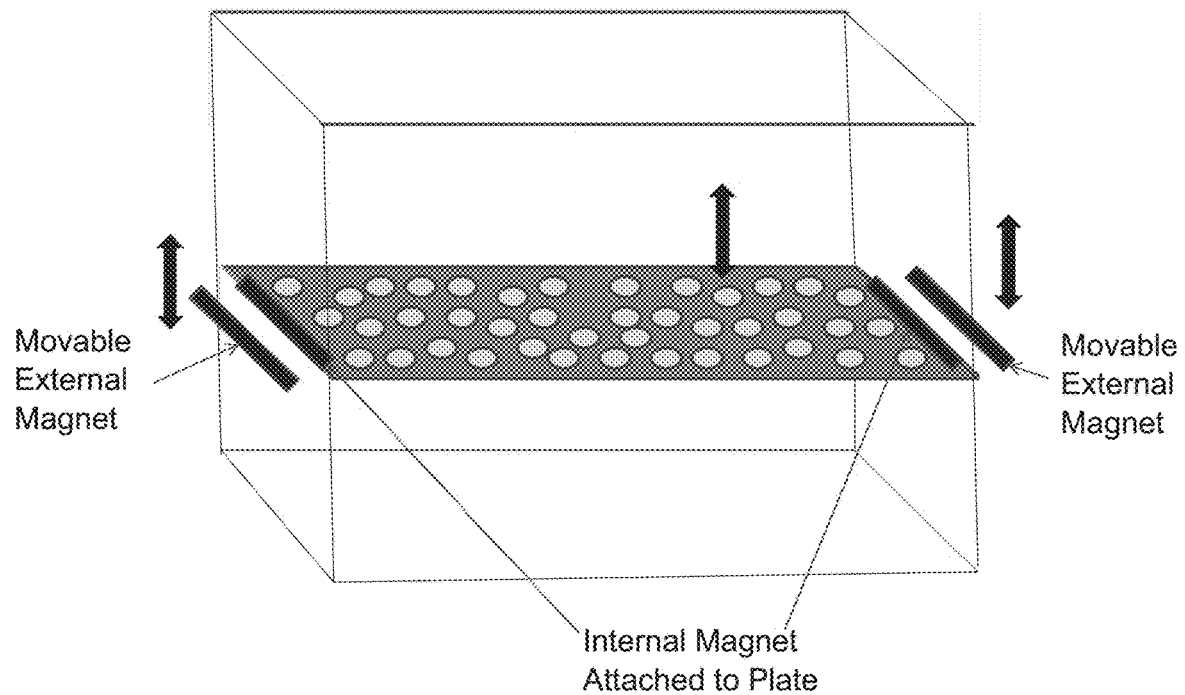
FIG. 6A shows a non-limiting schematic of an ADBR with a rectangular plate equipped with magnetic rods at opposite ends of the plate, where the upward or downward movement of corresponding external magnets move the plate accordingly along the axial direction of the bioreactor.
Figure 6B:
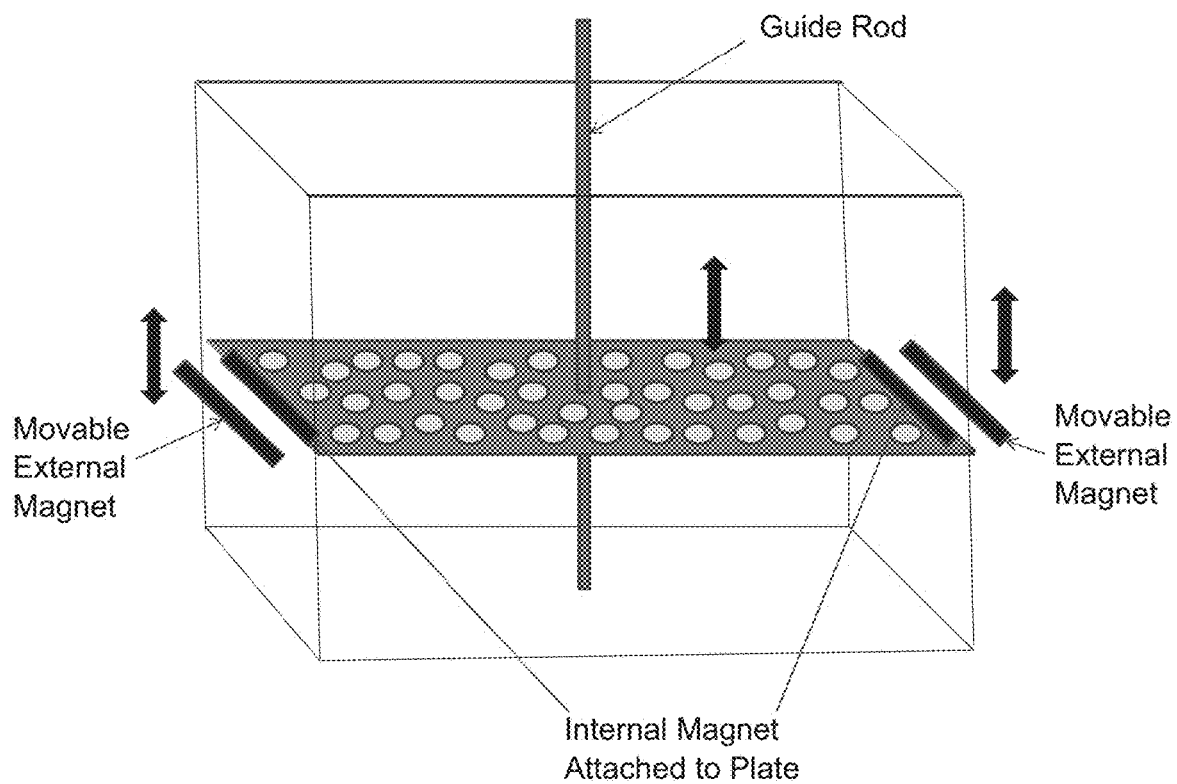
FIG. 6B shows a non-limiting schematic of the ADBR shown in FIG. 6A with the addition of a guide rod.
Figure 7:
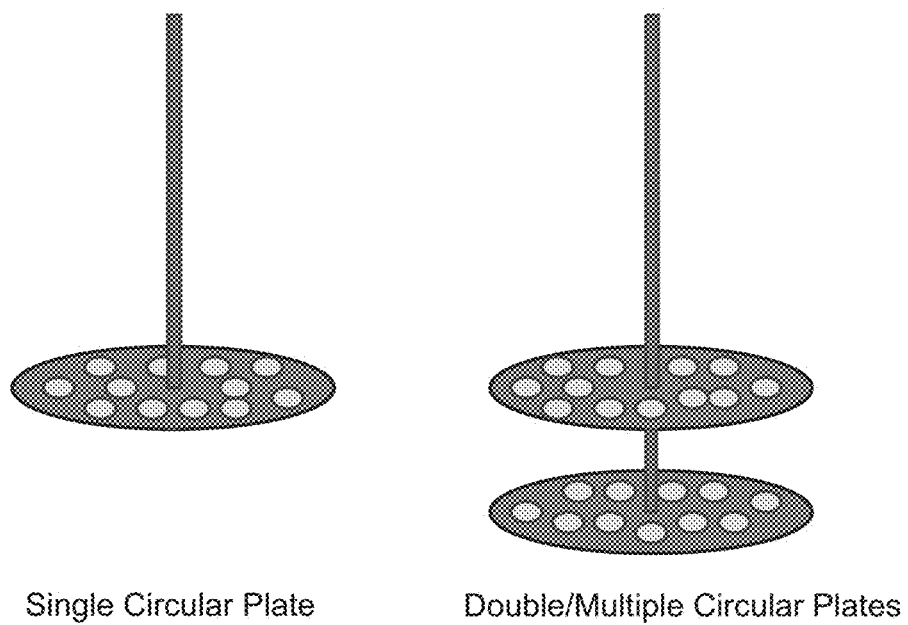
FIG. 7 shows a non-limiting schematic of single and double/multiple ADBR plates assuming circular and flat-surface geometric configurations.
Figure 8:
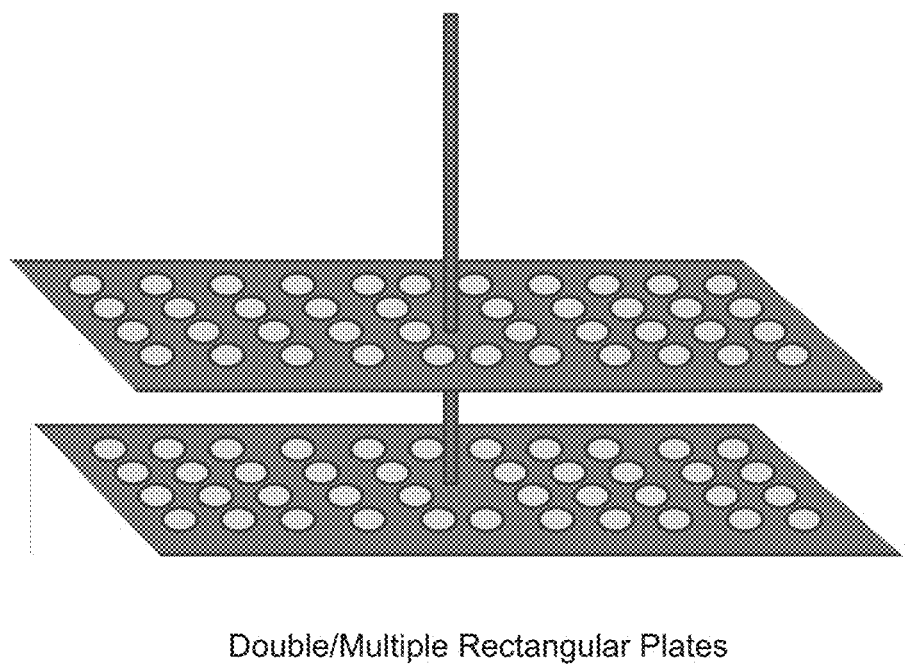
FIG. 8 shows a non-limiting schematic of double/multiple ADBR plates assuming rectangular and flat-surface geometric configurations.

Referring to FIG. 5, in another embodiment, the mechanism for the movement of the one or more mixing plates may comprise one or more pulleys which are turned by one or more external motors, wherein one or more belts are fixed to the one or more mixing plates, pass through the one or more pulleys, and move the one or more mixing plates longitudinally or axially within the vessel. According to other embodiments, as shown in FIGS. 6A-6B, the mechanism for the movement of the one or more mixing plates comprises two or more internal magnets attached to the one or more mixing plates and two or more movable exterior magnets on the other face of the one or more sidewalls, wherein movement of the exterior magnets moves the one or more mixing plates longitudinally or axially within the vessel. In one embodiment, the mechanisms described herein may cause the mixing plates to move vertically within the bioreactor. Alternatively, the mechanisms described herein may be oriented in some manner such that the mixing plates are configured to move laterally within the bioreactor.

In some embodiments, a single back-and-forth movement of the mixing plates is referred to herein as "stroke". In some embodiments, the mechanism may be capable of moving the mixing plates at a rate of about 1-10 strokes per minute, or about 10-50 strokes per minute, or about 50-100 strokes per minute, or about 100-150 strokes per minute, or about 150-200 strokes per minute.

In some embodiments, the bioreactor may comprise more than one mixing plate. As a non-limiting example, the bioreactor may comprise about 2-5, 5-10, 10-20 or 20-50 mixing plates. In other embodiments, the spacing between the mixing plates may be uniform or varied. As a non-limiting example, the spacing between the plates may be about 1-5 cm, or about 5-10 cm, or about 10-20 cm, or about 20-50 cm.

In other embodiments, the size of the through holes may be uniform or varied. As a non-limiting example, the size of the through holes may be about 1-5 cm, or about 5-10 cm, or about 10-20 cm, or about 20-50 cm. In yet other embodiments, the mixing plates may have a uniform or varied percentage of its total area comprised of the through holes. As a non-limiting example, a mixing plate may have about 1-10%, or about 5-20%, or about 15-30%, or about 25-40%, or about 30-50%, or about 40-60%, or about 50-70%, or about 60-80%, or about 75-90% of its total area comprised of the through holes.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. The reference numbers recited in the below claims are solely for ease of examination of this patent application, and are exemplary, and are not intended in any way to limit the scope of the claims to the particular features having the corresponding reference numbers in the drawings. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. A bioreactor system comprising:
   a. a bioreactor vessel (100) for containing a fluid, comprising one or more sidewalls (120);
   b. at least one mixing plate (130) comprising a surface having a plurality of holes (140) disposed through the surface, wherein the at least one mixing plate (130) extends up to and is constrained by the one or more sidewalls (120) of the bioreactor vessel (100);
   c. at least one vertical guide rod (150) configured to fit through one of the plurality of holes (140) in the at least one mixing plate (130); and
   d. a mechanism (160) for moving the at least one mixing plate (130) within the bioreactor vessel, wherein the movement of the at least one mixing plate (130) enables mixing of the fluid in the bioreactor vessel to generate a hydrodynamic flow pattern.

2. The system of claim 1, wherein the bioreactor vessel is an axial dispersion bioreactor tank.

3. The system of claim 1, wherein the surface of the at least one mixing plate (130) comprises a flat or curved surface.

4. A bioreactor system for the cultivation of biological cultures, the system comprising:
   a. a bioreactor vessel (100) for containing a liquid growth medium, comprising a bottom (110) and one or more sidewalls (120);
   b. one or more mixing plates (130), each comprising a plurality of through holes (140), wherein the one or more mixing plates (130) extend up to and are constrained by the one or more sidewalls (120) of the bioreactor vessel (100);
   c. one or more vertical guide rods (150) each configured to fit through one of the plurality of holes (140) in the one or more mixing plates (130); and
   d. a mechanism (160) for moving the one or more mixing plates longitudinally or axially within the bioreactor vessel;
      wherein the movement of the one or more mixing plates enables mixing of the liquid growth medium and generation of a hydrodynamic flow pattern.

5. The system of claim 4, wherein the one or more mixing plates each comprise a shape, wherein the shape is a circle, oval, ellipse, square, rectangle, parallelogram, quadrilateral, triangle, pentagon, hexagon, heptagon, octagon, polygon, or irregular shape.

6. The system of claim 4, wherein the one or more mixing plates each comprise a surface which is flat, rippled, textured, curved, concave, convex, zig-zag patterned, or has compound curves.

7. The system of claim 4, wherein the plurality of through holes each comprise a shape and a size, and wherein the shapes and sizes of the holes are either uniform or varied, wherein the shapes and sizes of the holes are configured to modify or enhance the hydrodynamic flow pattern or mixing of the liquid growth medium.

8. The system of claim 4, wherein the bioreactor comprises a plurality of rigid or flexible ribbons having two ends, wherein the ribbons are attached to the one or more mixing plates at one or both ends, wherein the rigid or flexible ribbons are configured to modify or enhance the hydrodynamic flow pattern or mixing of the liquid growth medium.

9. The system of claim 4, wherein the movement of the one or more mixing plates is continuous or intermittent back-and-forth axial displacement at a regulated variable rate.

10. The system of claim 4, wherein one or more gasses are sparged or bubbled through the liquid growth medium from the bottom of the bioreactor with a specified bubble size and a gas flow rate for each gas.

11. The system of claim 4, wherein the mechanism for the movement of the one or more mixing plates comprises one of the following mechanisms:
   i. a piston rod and crankshaft which connect the one or more mixing plates with an external motor, and wherein the piston rod moves the one or more mixing plates longitudinally or axially within the vessel;
   ii. the one or more guide rods comprise one or more threaded rods each threaded through one of the plurality of holes in the one or more mixing plates and are attached to one or more external motors;
   iii. one or more pulleys which are turned by one or more external motors, wherein one or more belts are fixed to the one or more mixing plates, pass through the one or more pulleys, and move the one or more mixing plates longitudinally or axially within the vessel; or
   iv. two or more internal magnets attached to the one or more mixing plates and two or more movable exterior magnets on the other face of the one or more sidewalls, wherein movement of the exterior magnets moves the one or more mixing plates longitudinally or axially within the vessel.

12. A method of promoting the growth and production of a biological culture contained in a bioreactor, the method comprising:
   a. providing a bioreactor, the bioreactor comprising:
      i. a bioreactor vessel (100), comprising a bottom (110) and one or more sidewalls (120);
      ii. one or more mixing plates (130), each comprising a plurality of through holes (140), wherein the one or more mixing plates (130) extend up to and are constrained by the one or more sidewalls (120) of the bioreactor vessel (100);
      iii. one or more vertical guide rods (150) each configured to fit through one of the plurality of holes (140) in the at least one mixing plate (130); and
      iv. a mechanism (160) for moving the one or more mixing plates longitudinally or axially within the bioreactor vessel;
   b. providing a biological culture, wherein the biological culture is dispersed within a liquid growth medium;
   c. adding the biological culture and liquid growth medium into the bioreactor; and
   d. moving the one or more mixing plates longitudinally or axially within the bioreactor vessel via the mechanism;
wherein the movement of the one or more mixing plates mixes the liquid growth medium and generates a hydrodynamic flow pattern.

13. The method of claim 12, wherein the one or more mixing plates each comprise a shape, wherein the shape is a circle, oval, ellipse, square, rectangle, parallelogram, quadrilateral, triangle, pentagon, hexagon, heptagon, octagon, polygon, or irregular shape.

14. The method of claim 12, wherein the one or more mixing plates each comprise a surface which is flat, rippled, textured, curved, concave, convex, zig-zag patterned, or has compound curves.

15. The method of claim 12, wherein the plurality of through holes each comprise a shape and a size, and wherein the shapes and sizes of the holes are either uniform or varied, wherein the shapes and sizes of the holes are configured to modify or enhance the hydrodynamic flow pattern or mixing of the liquid growth medium.

16. The method of claim 12, wherein the bioreactor comprises a plurality of rigid or flexible ribbons having two ends, wherein the ribbons are attached to the one or more mixing plates at one or both ends, wherein the rigid or flexible ribbons are configured to modify or enhance the hydrodynamic flow pattern or mixing of the liquid growth medium.

17. The method of claim 12, wherein the one or more mixing plates have a spacing which is configured to modify or enhance the hydrodynamic flow pattern or mixing of the liquid growth medium.

18. The method of claim 12, wherein the movement of the one or more mixing plates is continuous or intermittent back-and-forth axial displacement at a regulated variable rate.

19. The method of claim 12, wherein one or more gasses are sparged or bubbled through the liquid growth medium from the bottom of the bioreactor with a specified bubble size and a gas flow rate for each gas.

20. The method of claim 12, wherein the mechanism for the movement of the one or more mixing plates comprises one of the following mechanisms:
   i. a piston rod and crankshaft which connect the one or more mixing plates with an external motor, and wherein the piston rod moves the one or more mixing plates longitudinally or axially within the vessel;
   ii. the one or more guide rods comprise one or more threaded rods each threaded through one of the plurality of holes in the one or more mixing plates and are attached to one or more external motors;
   iii. one or more pulleys which are turned by one or more external motors, wherein one or more belts are fixed to the one or more mixing plates, pass through the one or more pulleys, and move the one or more mixing plates longitudinally or axially within the vessel; or
   iv. two or more internal magnets attached to the one or more mixing plates and two or more movable exterior magnets on the other face of the one or more sidewalls, wherein movement of the exterior magnets moves the one or more mixing plates longitudinally or axially within the vessel.

* * * * *